US00PP09608P

United States Patent [19]

Meilland

[11] Patent Number: Plant 9,608

[45] Date of Patent: Jul. 23, 1996

[54] HYBRID TEA ROSE PLANT NAMED 'MEIROMAR'

[75] Inventor: Alain A. Meilland, Antibes, France

[73] Assignee: The Conard-Pyle Company, West Grove, Pa.

[21] Appl. No.: 496,159

[22] Filed: Jun. 28, 1995

[51] Int. Cl.[6] ..... A01H 5/00

[52] U.S. Cl. ..... Plt./15

[58] Field of Search ..... Plt./15, 16, 22, Plt./24, 25

[56] References Cited

U.S. PATENT DOCUMENTS

P.P. 7,138 2/1990 Suzuki ..... Plt./18

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive Saffron Yellow blossoms that commonly exhibit a perfect shape when opening. Such blossoms are long-lasting when cut and placed in a vase and exhibit good petal-drop characteristics whereby the petals tend to detach cleanly. The plant is vigorous and exhibits attractive medium green foliage. The new variety is particularly well suited for cut flower production under greenhouse growing conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Meipierar' variety (U.S. Plant Pat. No. 7,622) variety. The male parent (i.e., the pollen parent) was the 'Keiromo' variety (U.S. Plant Pat. No. 7,138). The parentage of the new variety can be summarized as follows:

'Meipierar'×'Keiromo'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive long-lasting Saffron Yellow blossoms,
(b) forms vigorous vegetation,
(c) forms medium green foliage, and
(d) is particularly well suited for cut flower production.

The blossoms tend to possess a perfect shape at the opening which is well retained when the blossoms are cut and are placed in a vase. The perfect shape of the blossoms is manifest by the presence of nicely turbinated petals and a high center.

The new variety well meets the needs of the horticultural industry and is particularly well adapted for cut flower production under greenhouse growing conditions.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meiromar' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Cap d'Antibes, Var, France.

DETAILED DESCRIPTION

Figures 1, 2, 3, 4, 5, 6, 7, 8, 9, 10, 11, 12, 13, 14, 15:
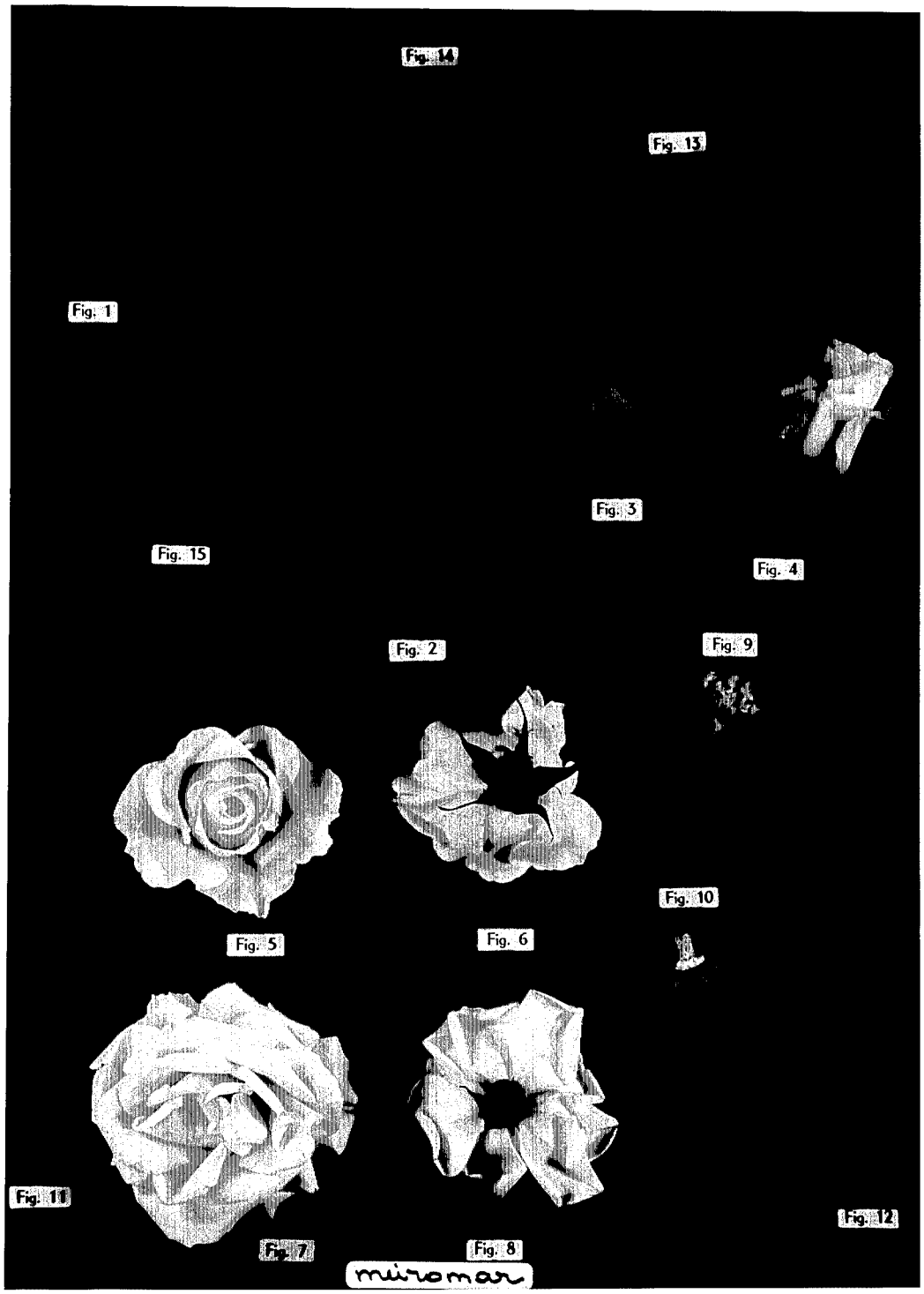
FIG. 1 illustrates a specimen of a young shoot.
FIG. 2 illustrates a specimen of a floral bud at the opening of the sepals.
FIG. 3 illustrates a specimen of a floral bud at the opening of the petals.
FIG. 4 illustrates a specimen of a flower in the course of opening.
FIG. 5 illustrates a specimen of an open flower—plan view—obverse.
FIG. 6 illustrates a specimen of an open flower—plan view—reverse.
FIG. 7 illustrates a specimen of a fully open flower—plan view—obverse.
FIG. 8 illustrates a specimen of a fully open flower—plan view—reverse.
FIG. 9 illustrates a specimen of a floral receptacle showing the arrangement of the stamens and pistils.
FIG. 10 illustrates a specimen of a floral receptacle showing the arrangement of the pistils (stamens removed)
FIG. 11 illustrates a specimen of a flowering stem.
FIG. 12 illustrates a specimen of a main branch.
FIG. 13 illustrates a specimen of a leaf with three leaflets—plan view—upper surface.
FIG. 14 illustrates a specimen of a leaf with five leaflets—plan view—under surface.
FIG. 15 illustrates a specimen of a leaf with seven leaflets—plan view—upper surface.

The chart used in the identification of the colors is that of The Royal Horticultural Society (R.H.S. Colour Chart). The description is based on the observation of two year-old plants while budded on *Rosa indica* understock and growing in greenhouses at Cap d'Antibes, France. The coloration in common terms precedes reference to the chart.

Class: Hybrid Tea.

Plant:

*Height.*—When pruned to a height of 0.85 m., floral stems of approximately 40 to 70 cm. in length commonly are produced.

*Habit.*—Erect.

Branches:

*Color.*—Young stems: medium green, Green Group 143A. Adult wood: dark green, Green Group 137A.

*Thorns.*—Size: medium. Quantity: numerous. Color: greenish on young stems and greenish-pinkish on adult wood.

Leaves:

*Stipules.*—Adnate, pectinate, and very large and linear.

*Petioles.*—Upper surface: striped reddish brown on young foliage, and medium green on adult foliage with more or less glandular edges. Under surface: bear a few small thorns.

*Leaflets.*—Number: 3, 5 (most often), and 7. Shape: oval. Serration: simple and regular. Texture: consistent. General appearance: dense, and semi-dull foliage. Color (young foliage): Upper surface: medium green, Green Group 137B. Under surface: light green, Green Group 137C, suffused with grayish-green, Greyed-Green Group 191A. Color (adult foliage): Upper surface: medium green, Green Group 137B, and more or less suffused with dark green, Green Group 139B. Under surface: light green, Green Group 137C.

Inflorescence:

*Number of flowers.*—Usually one per stem, but sometimes up to approximately 3 flowers per stem. The flower productivity commonly is approximately 100 to 150 flowers/m.$^2$ when grown under greenhouse conditions at a rate of 6½ to 7 plants/m$^2$.

*Peduncle.*—Medium green, smooth, and sometimes bears small thorns. The length is approximately 8 to 10 cm. on average.

*Sepals.*—Upper surface: tomentose, and medium green in coloration, and possess foliar appendages. Under surface: light green and the edges are more or less glandular.

*Buds.*—Shape: conical. Length: approximately 2.5 to 3 cm. on average. Size: medium. Color upon opening: Upper surface: Saffron Yellow, Yellow-Orange Group 19B commonly with a light greenish hue on external petals. Under surface: Saffron Yellow, Yellow-Orange Group 19B, and suffused with light Apricot Orange, Orange Group 24D.

*Flower.*—Shape: cupped with a high center, and often exhibits a round heart. Diameter: approximately 10 cm. on average. Color (when opening begins): Upper surface: Saffron Yellow, Yellow-Orange Group 19B commonly with a light greenish hue on external petals. Under surface: Saffron Yellow, Yellow-Orange Group 19B, commonly with a light greenish hue on external petals. Color (when blooming): Upper surface: 16D Yellow-Orange Group. Under surface: 16D with whitening, Yellow-Orange Group. Color (at end of opening): Upper surface: between Yellow-Orange Group 19C and 19D. Under surface: between Yellow-Orange Group 19C and 19D. Fragrance: none. Lasting quality: very long when cut and placed in vase. Blossoms commonly last approximately 8 to 10 days on average when cut and placed in a vase and approximately 7 to 9 days on average on the plant. Petal shape: rounded and when the flower is fully open the edges commonly are reflexed. Petal number: approximately 30 on average. Petal drop: good whereby the petals tend to detach cleanly. Stamen number: approximately 220 on average. Petal number: approximately 30 on average. Anthers: normal and ochre in coloration. Filaments: bright yellow in coloration. Pistils: approximately 141 on average. Stigmas: Normal strawlike in coloration (i.e., possess coloration between light yellow and light green). Styles: tomentose at base, light fuchsine in coloration, and commonly fused together. Receptacle: medium green, and in longitudinal section in the shape of a wide pitcher. Hips and seeds: are formed.

Development:

*Vegetation.*—Vigorous.

*Blooming.*—Abundant.

*Resistance to diseases.*—Very good.

I claim:

1. A new and distinct variety of Hybrid Tea rose plant characterized by the following combination of characteristics:

(a) forms in abundance attractive long-lasting Saffron Yellow blossoms,
(b) forms vigorous vegetation,
(c) forms medium green foliage, and
(d) is particularly well suited for cut flower production;

substantially as herein shown and described.

* * * * * miramar